(12) United States Patent
Weiss

(10) Patent No.: US 10,258,766 B2
(45) Date of Patent: Apr. 16, 2019

(54) TUBE FOR BEING INTRODUCED INTO AN OBJECT

(71) Applicant: KONINKLIJKE PHILIPS N.V., Eindhoven (NL)

(72) Inventor: Steffen Weiss, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 894 days.

(21) Appl. No.: 14/360,833

(22) PCT Filed: Nov. 29, 2012

(86) PCT No.: PCT/IB2012/056822
§ 371 (c)(1),
(2) Date: May 27, 2014

(87) PCT Pub. No.: WO2013/080151
PCT Pub. Date: Jun. 6, 2013

(65) Prior Publication Data
US 2014/0330253 A1 Nov. 6, 2014

Related U.S. Application Data

(60) Provisional application No. 61/564,325, filed on Nov. 29, 2011.

(51) Int. Cl.
*A61M 25/00* (2006.01)
*D04C 1/02* (2006.01)
*A61M 25/01* (2006.01)

(52) U.S. Cl.
CPC .............. *A61M 25/005* (2013.01); *D04C 1/02* (2013.01); *A61M 25/0054* (2013.01);
(Continued)

(58) Field of Classification Search
CPC ............ A61M 25/005; A61M 25/0012; A61M 25/0053
See application file for complete search history.

(56) References Cited

U.S. PATENT DOCUMENTS 6,004,310 A * 12/1999 Bardsley ........... A61M 25/0009
604/524
6,605,944 B2 8/2003 Engelke
(Continued)

FOREIGN PATENT DOCUMENTS

| EP | 0702976 A1 | 3/1996 |
|----|------------|--------|
| WO | 2010102122 A1 | 9/2010 |
| WO | 2011081713 A1 | 7/2011 |

OTHER PUBLICATIONS

Krueger S, Lips O, David B, Weiss S. A Novel Broad-band, High Power and RF-safe Cable for MR-guided Catheter Ablation. In: Proceedings of the 19th Scientific Meeting of the ISMRM, Montreal, Canada; 2011. p. 3755.

*Primary Examiner* — Emily Schmidt

(57) ABSTRACT

The application relates to a tube for being introduced into an object. The tube (1), which is preferentially a catheter, comprises a tube-like braid (2) made from electrically conductive strands (3), wherein ends (4) of the strands (3) are staggered in the longitudinal direction of the tube (1). Since the ends of the strands are staggered in the longitudinal direction of the tube, local radio frequency heat generated during a magnetic resonance imaging procedure is not concentrated at a single longitudinal location, but distributed along a staggered region in the longitudinal direction of the tube, in which the ends of the electrically conductive strands are staggered. This distribution of the radio frequency heat along the longitudinal direction of the tube reduces the maximum temperature produced by radio (Continued)

frequency heating and, thus, the likelihood of damaging the object, in which the tube is to be introduced, due to heat.

17 Claims, 5 Drawing Sheets

(52) U.S. Cl.
CPC . *A61M 25/0127* (2013.01); *A61M 2025/0059* (2013.01); *A61M 2205/0233* (2013.01); *D10B 2101/12* (2013.01); *D10B 2101/20* (2013.01); *D10B 2401/18* (2013.01); *D10B 2509/00* (2013.01)

(56) References Cited

U.S. PATENT DOCUMENTS

| | | |
|---|---|---|
| 2005/0137519 A1 | 6/2005 | Boismier |
| 2008/0243218 A1 | 10/2008 | Bottomley |
| 2008/0251966 A1 | 10/2008 | Kampa |
| 2009/0149920 A1 | 6/2009 | Li |
| 2009/0270839 A1 | 10/2009 | Warnock |
| 2010/0000780 A1 | 1/2010 | Zhu |

\* cited by examiner

TUBE FOR BEING INTRODUCED INTO AN OBJECT

CROSS-REFERENCE TO PRIOR APPLICATIOINS

This application is the U.S. National Phase application under 35 U.S.C. § 371 of International Application No. PCT/IB2012/056822, filed on Nov. 29, 2012, which claims the benefit of U.S. Provisional Patent Application No. 61/564,325, filed on Nov. 29, 2011. These applications are hereby incorporated by reference herein.

FIELD OF THE INVENTION

The invention relates to a tube for being introduced into an object, in particular, to a catheter. The invention relates further to a manufacturing apparatus and a manufacturing method for manufacturing the tube, and an interventional system and an interventional method for performing an interventional procedure using the tube.

BACKGROUND OF THE INVENTION

Conventional catheters are generally equipped with a wire braid made from individual mechanically very strong and therefore usually metallic strands to achieve high torque transmission and high kink resistance. However, such conductive wire braids are prohibitive in magnetic resonance imaging due to radio frequency heating which may occur at the end of the wire braid.

SUMMARY OF THE INVENTION

It is an object of the present invention to provide a tube for being introduced into an object, which produces heat having a reduced maximum temperature, when used in a magnetic resonance imaging system. It is a further object of the present invention to provide a manufacturing apparatus and a manufacturing method for manufacturing the tube, and an interventional system and an interventional method for performing an interventional procedure using this tube.

In a first aspect of the present invention a tube for being introduced into an object is presented, wherein the tube comprises a tube-like braid made from electrically conductive strands, wherein ends of the strands are staggered in the longitudinal direction of the tube.

Since the ends of the strands are staggered in the longitudinal direction of the tube, local radio frequency heat generated during a magnetic resonance imaging procedure is not concentrated at a single longitudinal location, but distributed along a staggered region in the longitudinal direction of the tube, in which the ends of the electrically conductive strands are staggered. This distribution of the radio frequency heat along the longitudinal direction of the tube reduces the maximum temperature produced by radio frequency heating and, thus, the likelihood of damaging the object, in which the tube is to be introduced, due to heat.

The tube is preferentially adapted to be introduced into a living being like a person or an animal for performing an interventional procedure. The tube is, for example, a catheter or an introducer sheath. The strands have preferentially different lengths for staggering the ends of the strands in the longitudinal direction.

In a preferred embodiment, the ends of the strands are staggered in a stagger region, wherein the stagger region is located at or adjacent to an end of the tube. In particular, the stagger region is preferentially located at or close to a distal tip of the tube. In an embodiment, the braid ends close to, but proximal to the distal tip of the tube, in order to allow for a more floppy distal tube section, in order to further reduce the likelihood of, in particular, avoid, damages to the object, wherein in the stagger region at the braid end the maximal temperature is reduced due to the staggered ends of the individual strands.

It is further preferred that the ends of the strands are staggered in a stagger region, wherein the stagger region has a length within a range of 2 cm to 10 cm. A stagger region having this length provides a significant reduction in the temperature generated by radio frequency heating, while a sufficient high torque transmission and kink resistance can still be provided.

In an embodiment, end sections of at least some strands traverse the tube towards the center of the tube. In particular, the end sections of all strands traverse the tube towards the center line of the tube. In a further preferred embodiment, the ends of at least some strands are arranged at or adjacent to, i.e near, the center of the tube. If the ends of at least some strands are arranged more to the center of the tube, in particular, if all ends of the strands are arranged more to the center of the tube, the distance between the location of the ends of the strands and the outside of the tube is increased, thereby further reducing the temperature outside of the tube generated by radio frequency heating.

It is further preferred that the braid is arranged within a tube material enclosing an inner lumen of the tube. The inner lumen can be adapted to, for example, guide an element located within the inner lumen to a desired location within an object, provide a cooling fluid and/or receive a guide wire for guiding the tube within the object.

The tube material comprises preferentially an elastic biocompatible material like a biocompatible polymer.

It is further preferred that the ends of at least some of the strands are arranged adjacent to the inner lumen. It is also preferred that the ends of at least some of the strands are inserted into the lumen. The inner lumen can function as a heat sink, in particular, if cooling fluid is present in the inner lumen, thereby further reducing the temperature generated by radio frequency heating, if the ends of the strands are located adjacent to the inner lumen or are introduced into the inner lumen. In particular, the inner lumen, in which the ends of at least some of the strands can be inserted, can be an irrigation lumen.

In a further embodiment the strands are made of a non-magnetic material. The non-magnetic material can be nitinol or another non-magnetic material. This allows reducing, in particular preventing, magnetic forces which may act on the tube during magnetic resonance imaging.

The strands can comprise at least one of metal and carbon. For instance, the strands can be metallic strands or they can be carbon fibers.

The strands can comprise at least two electrically conductive materials, in particular, at least two metals, a first electrically conductive material providing a smaller stiffness of the respective strand and forming the ends of the strands and a second electrically conductive material providing a larger stiffness of the respective strand and forming the remaining part of the respective strand. Since the first electrically conductive material, which forms the ends of the strands, provides a smaller stiffness, specific routings of the ends of the strands may be easier realized during manufacturing the tube. Moreover, the likelihood of loosening of strands, which may cause damage inside the tube or even outside the tube, for example, upon sharp deflection of the tube, may also be decreased.

In a further aspect of the present invention an interventional system for performing an interventional procedure is presented, wherein the interventional system comprises a tube as defined in claim 1, wherein the tube is adapted to be introduced into an object for performing the interventional procedure.

In a further aspect of the present invention, an interventional method for performing an interventional procedure is presented, wherein the interventional method comprises introducing a tube as defined in claim 1 into an object for performing the interventional procedure.

In a further aspect of the present invention, a manufacturing apparatus for manufacturing a tube is presented, wherein the manufacturing apparatus comprises a strands providing unit for providing electrically conductive strands and a braiding unit for braiding the strands to a tube-like braid made such that ends of the strands are staggered in the longitudinal direction of the tube to be manufactured.

In a further aspect of the present invention, a manufacturing method for manufacturing a tube is presented, wherein the manufacturing method comprises a step of forming a tube-like braid made from electrically conductive strands such that ends of the strands are staggered in the longitudinal direction of the tube to be manufactured.

It shall be understood that the tube of claim 1, the interventional system of claim 12, the interventional method of claim 13, the manufacturing apparatus of claim 14 and the manufacturing method of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
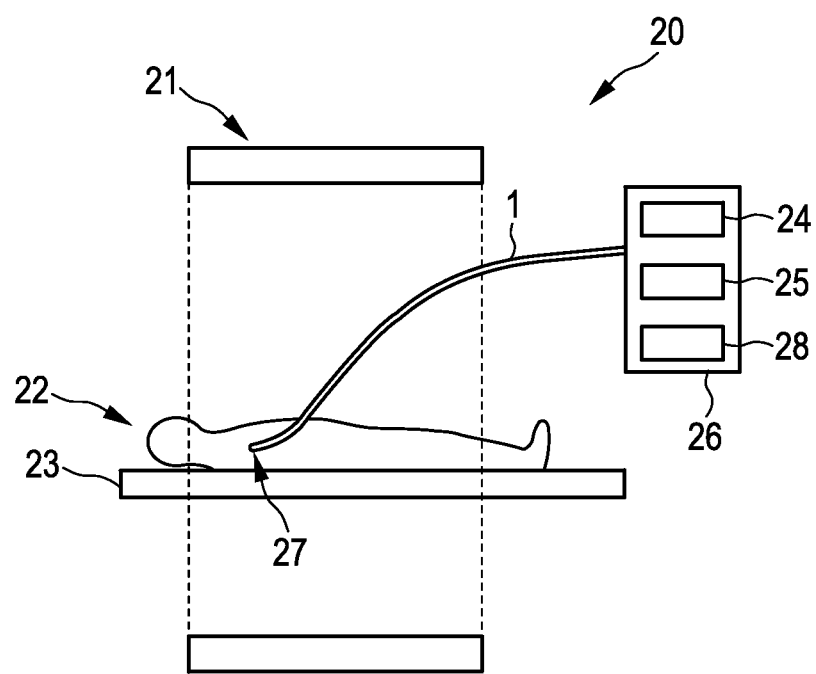
FIG. 1 shows schematically and exemplarily an embodiment of an interventional system for performing an interventional procedure.

FIG. 1 shows schematically and exemplarily an embodiment of an interventional system for performing an interventional procedure. The interventional system 20 comprises a catheter 1, which has been introduced into a person 22 lying on a table 23. The catheter 1, in particular, the catheter tip 27, is imaged or localized within the person 22 by using a magnetic resonance imaging system 21. The catheter 1 is connected to a catheter control unit 26 comprising an energy application unit 24, a measurement unit 28 and an irrigation fluid providing unit 25. The energy application unit 24 and the catheter 1 can be adapted to apply, for example, radiofrequency energy, optical energy or another kind of energy within the person 22 for performing, for instance, an ablation procedure. The measurement unit 28 and the catheter 1 can be adapted to measure the position of the catheter, and physiological quantities like temperature, pressure, or blood flow inside the person 22. Moreover, the catheter 1 and the irrigation fluid providing unit 25 can be adapted to allow a cooling fluid to flow through the catheter 1 for cooling the catheter tip 27 within the person 22.

Figure 2:
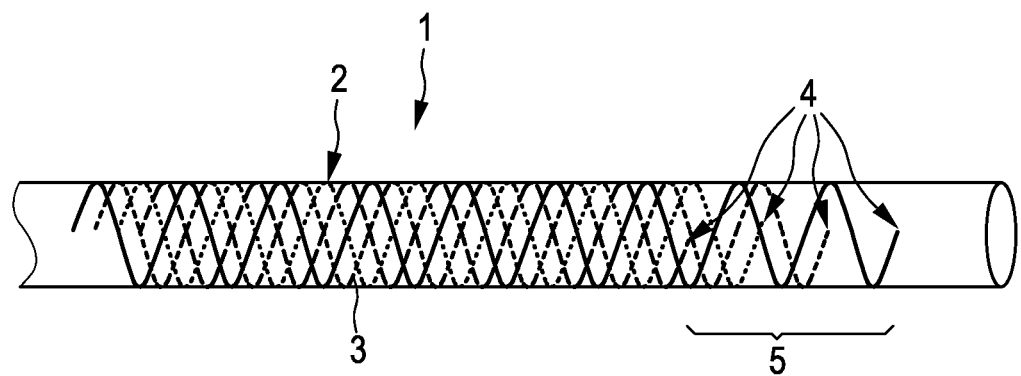
FIGS. 2 to 5 show schematically and exemplarily embodiments of a catheter.

The catheter 1 is a tube for being introduced into the person 22 and comprises a tube-like braid 2 made from electrically conductive strands 3, wherein ends 4 of the strands 3 are staggered in the longitudinal direction of the tube. In this embodiment, the electrically conductive strands 3 are metallic strands. The braid 2 is schematically and exemplarily shown in more detail in FIG. 2.

The strands 3 have different lengths for staggering the ends 4 of the strands 3 in the longitudinal direction in a stagger region 5, which is located at or close to the distal end of the catheter 1, i.e. close to the catheter tip 27, and which has a length within a range of 2 cm to 10 cm. Further elements of the catheter 1 like electrical or optical connections for applying energy, which is, for example, radiofrequency energy or optical energy, and/or for measurement purposes, a cooling fluid lumen et cetera are standard elements, which are known to the person skilled in the art and which are not shown in FIG. 2 for clarity reasons. In fact, the catheter can be similar to a standard catheter, wherein instead of a standard braid the tube-like braid 2 made from the electrically conductive strands 3 having ends 4 staggered in the longitudinal direction of the catheter 1 is used.

Figure 3:
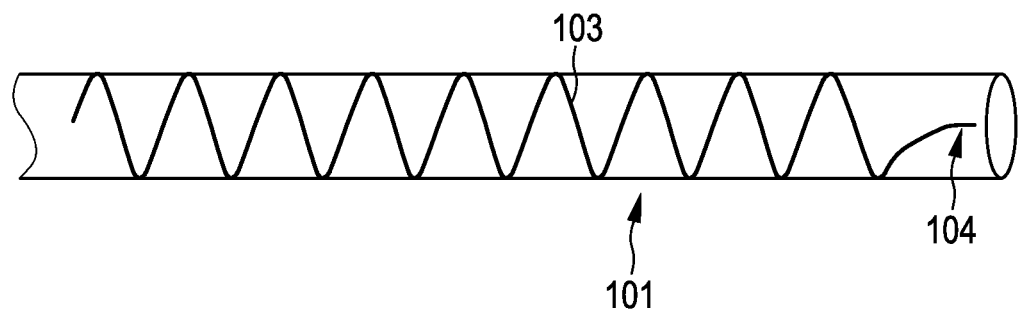

FIG. 3 illustrates a further embodiment of a catheter comprising a tube-like braid made from electrically conductive strands being, in this embodiment, metallic strands, wherein the ends of the strands are staggered in the longitudinal direction of the catheter. In FIG. 3, only one strand 103 of the tube-like braid within the catheter 101 is shown for clarity reasons. In particular, also the catheter 101 comprises further strands forming the tube-like braid and further standard elements for performing a desired interventional procedure.

The strand 103 shown in FIG. 3 comprises an end section with an end 104, which traverses the tube 101 towards the center of the tube 101. In this embodiment, the end section of all strands of the tube-like braid traverse the tube towards the center line of the tube 101 as exemplarily shown in FIG. 3 for a single strand. The tips of the end sections, i.e. the ends themselves, can be located at the center line of the tube.

Figure 4:
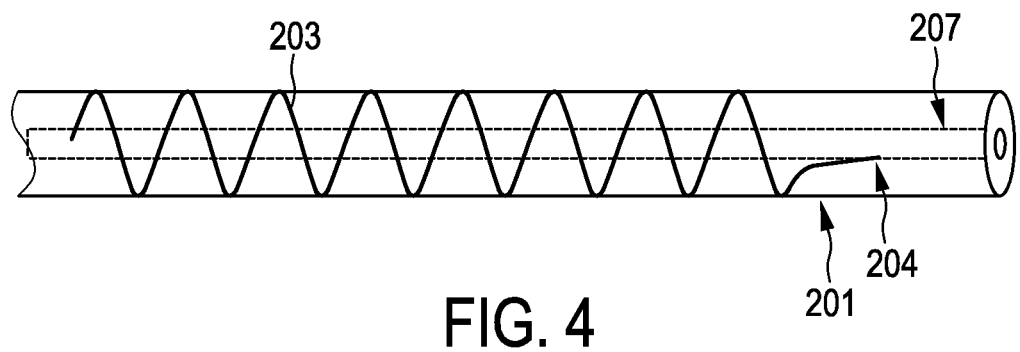

In an embodiment, the catheter comprises one or several inner lumina, wherein the one or several inner lumina are enclosed by tube material, in which the braid is arranged. An inner lumen can be adapted to, for example, guide an element located within the inner lumen to a desired location within an object like the person 22, to provide a cooling fluid and/or to receive a guide wire for guiding the catheter within the object. The tube material is preferentially an elastic biocompatible material like a biocompatible polymer. The ends 204 of the strands 203 can be arranged adjacent to the inner lumen 207 of the catheter 201 as schematically and exemplarily shown in FIG. 4. Also in FIG. 4 only a single strand of the tube-like braid is shown, and standard catheter elements and the entire braid are not shown for clarity reasons.

Figure 5:
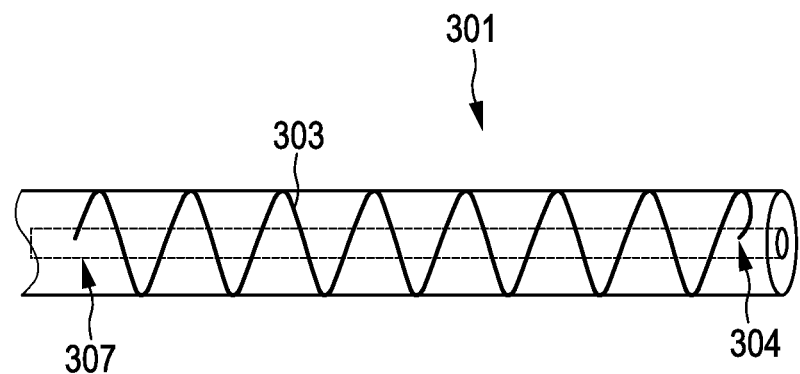

Ends 304 of strands 303 can also be inserted into an inner lumen 307 of a catheter 301 as schematically and exemplarily shown in FIG. 5. Also in FIG. 5 only a single strand is shown for clarity reasons, although the catheter 301 comprises further strands forming the tube-like braid and may comprise further standard elements of a catheter like electrical connections for providing electrical energy, optical fibers for providing optical energy, further lumina, et cetera.

The strands can be made of a non-magnetic material, in particular, of nitinol.

The strands can comprise at least two electrically conductive materials. In particular, the strands can comprise at least two metals, a first metal providing a smaller stiffness of the respective strand and forming the end sections of the strands, and a second metal providing a larger stiffness of the respective strand and forming the remaining part of the respective strand. The first metal is, for example, a thin copper cable, which is electrically connected to a respective end of the second metal providing the larger stiffness. The second metal providing the larger stiffness is, for example, nitinol. The at least two different electrically conductive materials can also be different kinds of carbon fibers. Or, a first electrically conductive material can be metal and a second electrically conductive material can be carbon fiber material or vice versa.

Figure 6:
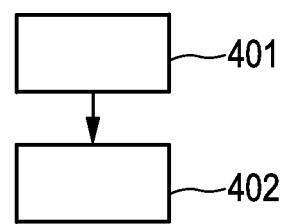
FIG. 6 shows a flowchart exemplarily illustrating an embodiment of an interventional method for performing an interventional procedure.

In the following an embodiment of an interventional method for performing an interventional procedure will exemplarily be described with reference to a flowchart shown in FIG. 6.

In step 401, a tube, for example, one of the above mentioned catheters, is introduced into a person, and, in step 402, a sensing and/or influencing step is performed by using the introduced tube. For instance, the tube can be adapted to perform an optical, electrical, ultrasound et cetera sensing and/or the tube can be adapted to perform an ablation procedure, wherein tissue within the person can be sensed and/or ablated by using the tube. During the interventional procedure a magnetic resonance imaging system can be used for locating the tube within the person, wherein due to the staggered ends of the strands of the tube-like braid the temperature generated by radio frequency heating can be reduced.

Figure 7:
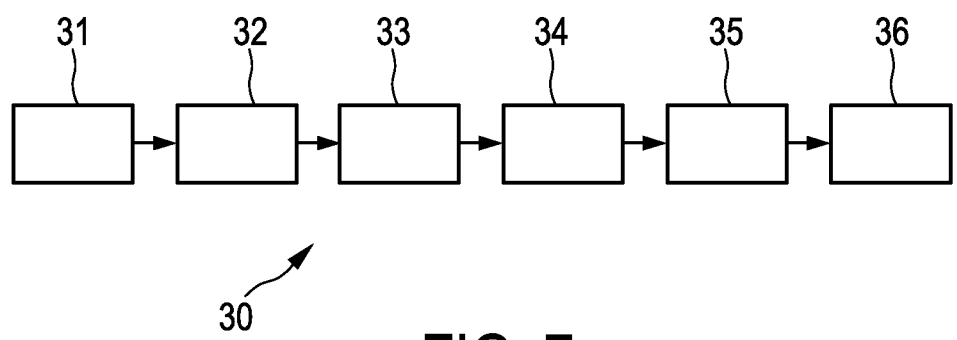
FIG. 7 shows schematically and exemplarily an embodiment of a manufacturing apparatus for manufacturing a tube.
Figure 8:
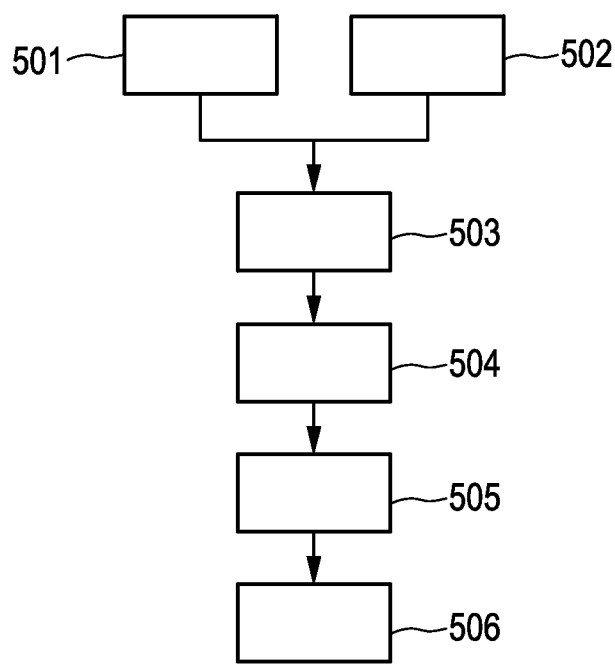
FIG. 8 shows a flowchart exemplarily illustrating an embodiment of a manufacturing method for manufacturing a tube.

FIG. 7 shows schematically and exemplarily an embodiment of a manufacturing apparatus for manufacturing a tube, and FIG. 8 shows a flowchart exemplarily illustrating a corresponding embodiment of a manufacturing method for manufacturing the tube.

The manufacturing apparatus 30 comprises an inner tube providing unit 31 for providing an inner tube having, for instance, one or several inner lumina in step 501. The inner tube providing unit 31 is, for example, a storage unit, in which at least one inner tube is stored for providing the same. The manufacturing apparatus further comprises a strands providing unit 32 for providing electrically conductive strands being, in this embodiment, metallic strands in step 502. Also the strands providing unit 32 can be a storage unit, wherein in this storage unit a plurality of metallic strands is stored for providing the same. In step 503, a braiding unit 33 winds the provided metallic strands onto the outside of the provided inner tube such that ends of the strands are staggered in the longitudinal direction of the tube to be manufactured. In particular, the braiding unit 33 can be adapted to cut the provided metallic strands such that they have different lengths, which lead, after the strands have been braided, to staggered ends in the longitudinal direction of the tube. This cutting of the metallic strands can also be performed by an additional cutting unit or by the strands providing unit 32. In step 504, an outer tube providing unit 34 provides an outer tube with an inner lumen, in which the inner tube with the tube-like braid is to be arranged. Also the outer tube providing unit can be a storage unit, in which at least one outer tube is stored for providing the same. In step 505, an outer tube applying unit 35 applies the provided outer tube on top of the braid on the inner tube, and, in step 506, a heating unit 36 heats the inner tube and the outer tube to allow partial melting of these tubes such that the braid is fixated.

Although the above described manufacturing apparatus 30 comprises a braiding unit, optionally a cutting unit and an outer tube applying unit, in other embodiments at least one of the corresponding steps can be performed manually such that the manufacturing apparatus does not need to comprise the respective units. For instance, the cutting of the strands and/or the application of the outer tube can be performed manually.

Although in the above described embodiment of manufacturing a tube the metallic strands are cut such that they have different lengths, in another embodiment soft metal ends can be applied to the ends of the metallic strands, wherein the soft metal ends have different lengths such that the lengths of the total resulting strands are different, and wherein these strands, after they have been braided, lead to staggered ends in the longitudinal direction of the tube.

The manufacturing apparatus 30 can comprise further units for, for instance, arranging electrical wires or optical fibers through the inner lumina of the tube, or, if desired, they can be arranged within the inner lumina manually. Moreover, inner lumina can be used for irrigation purposes or for receiving a guide wire.

The individual strands of known metallic catheter braids commonly all end at one point along the catheter and the entire braid is only covered by a thin coating such that tissue adjacent to the end zone, where the strands end, is prone to radio frequency tip heating. In the above described embodiments the ends have a special configuration, i.e. each end is cut to a different length so that the ends are staggered along the catheter over preferentially 2 cm to 10 cm, in order to avoid a concentrated local radio frequency heating. This effectively distributes any radio frequency heating along the length direction of the catheter. Moreover, preferentially the catheter is constructed such that each end section of the strands traverses to the center line of the catheter, thereby effectively increasing the insulation thickness around the end. Since the power density of magnetic resonance induced tip heating drops off rapidly in the order of $r^{-2}$ to $r^{-4}$ with distance r from the conductor tip, radio frequency heating of body tissue is minimized.

Known wire braids are often applied to a catheter shaft followed by a non-braided and therefore more floppy distal end section of the catheter. This avoids vessel injury and improves steerability. In the above described embodiments, the ends of the strands are staggered, which has the positive side effect that the commonly hard stepwise transition from the more rigid braided section to the unbraided floppy section is avoided in favor of a continuous transition of bending stiffness of the catheter. Moreover, since the strands are preferentially made of a non-magnetic material like nitinol, any magnetic forces can be avoided.

The catheter can be an irrigated radio frequency ablation catheter, in particular, for being used in cardiac electrophysiology interventions. The catheter can be equipped with tip irrigation, in particular, for cooling purposes, by fluids, mainly to avoid overheating and charring of tissue next to the tip, and in return to allow for more radio frequency power to create deeper ablation lesions in less time without those undesirable effects. The ablation catheter is equipped with a wire braid to enable sufficient steerability which is mandatory for electrophysiology procedures. For use in magnetic resonance imaging the ends of the strands of the braid are mounted closely to an inner irrigation channel or even inserted into this channel as schematically and exemplarily shown in FIGS. 4 and 5. The ends of the strands of the wire braid are staggered in the longitudinal direction of the ablation catheter. Already low infusion rates which are physiologically well-tolerated can cool off the heat produced during high specific absorption rate sequences.

In a further embodiment, the catheter has a center lumen to take up a guide wire for catheter guidance. The ends of the strands of the catheter braid are mounted directly adjacent to that lumen as exemplarily and schematically shown in FIG. 4. If the lumen is not occupied by a guide wire, the lumen can be irrigated with a slow saline infusion to cool off any heat during application of sequences with high specific absorption rate. If the lumen is occupied by a guide wire, which is preferentially electrically non-conductive, in order to be usable in magnetic resonance imaging, the guide wire replaces any water, which also avoids radio frequency heating. In terms of radio frequency safety, this situation corresponds to a catheter without lumen.

The ends of the strands can be formed by a conductive wire like a thin copper cable, which prolong the strands which may be made of a relatively stiff standard strand material like nitinol and which may be connected to the ends of these strands having the relatively stiff standard material. Since in this embodiment the ends are formed by the much more flexible, but still conductive wire, a specific routing as, for example, schematically and exemplarily shown in FIG. 4 can be realized much easier during manufacturing due to the high flexibility of the end wires, while the radio frequency safety properties can be maintained. Additionally, any conventional fixation of the stiff strands can be maintained as in standard catheter design, while only the flexible wires, in particular, the flexible copper cables, are staggered. This can reduce the likelihood that strands loosen and cause damage inside the catheter or even outside upon, for example, sharp deflection of the catheter.

The catheter with the staggered ends of the strands of the braid only requires relatively simple and cheap to implement modifications of standard devices.

Although in the above described embodiments the tube for being inserted into an object is a catheter, the tube can also be another kind of tube like an introducer sheath, in particular, for being used in interventional magnetic resonance imaging.

Although in above described embodiments the electrically conductive strands are metallic strands, the strands can also be made of another electrically conductive material. For instance, they can be made of carbon fibers.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

The provision of the strands, the cutting procedure, the braiding procedure, the application of the outer tube on the braid, the heating for partially melting the inner tube and the outer tube, et cetera performed by one or several units or devices can be performed by any other number of units or devices or manually. The control of the manufacturing apparatus in accordance with the manufacturing method and/or the control of the interventional system in accordance with the interventional method can be implemented as program codes means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A tube for being introduced into an object, the tube comprising:
a tube-like braid made from electrically conductive strands, wherein
ends of the strands are staggered in a longitudinal direction of the tube.

2. The tube as defined in claim 1, wherein the ends of the strands are staggered in a stagger region, wherein the stagger region has a length within a range of 2 cm to 10 cm.

3. The tube as defined in claim 1, wherein end sections of at least some strands traverse the tube towards the center of the tube.

4. The tube as defined in claim 3, wherein the ends of at least some strands are arranged at or adjacent to the center of the tube.

5. The tube as defined in claim 1, wherein the braid is arranged within a tube material enclosing an inner lumen of the tube.

6. The tube as defined in claim 5, wherein the ends of at least some of the strands are arranged adjacent to the inner lumen.

7. The tube as defined in claim 5, wherein the ends of at least some of the strands are inserted into the lumen.

8. The tube as defined in claim 1, wherein the strands are made of a non-magnetic material.

9. The tube as defined in claim 1, wherein the strands comprise at least one of metal and carbon.

10. The tube as defined in claim 1, wherein the strands comprise at least two electrically conductive materials:
a first electrically conductive material providing a smaller stiffness of the respective strand and forming the ends of the strands, and
a second electrically conductive material providing a larger stiffness of the respective strand and forming the remaining part of the respective strand.

11. The tube as defined in claim 1, wherein the tube is a catheter or an introducer sheath.

12. The tube of claim 1, wherein the ends of the strands have less stiffness than the remainder of the strands.

13. The tube of claim 1, wherein the ends of the strands are a different material than the remainder of the strands.

14. The tube of claim 1, wherein the strands are carbon.

15. An interventional system for performing an interventional procedure, wherein the interventional system comprises a tube as defined in claim 1, wherein the tube is adapted to be introduced into an object for performing the interventional procedure.

16. A manufacturing apparatus for manufacturing a tube as defined in claim 1, wherein the manufacturing apparatus comprises a strands providing unit for providing electrically conductive strands, wherein the manufacturing apparatus further comprises a braiding unit for braiding the strands to a tube-like braid made such that ends of the strands are staggered in the longitudinal direction of the tube to be manufactured.

17. A manufacturing method for manufacturing a tube as defined in claim 1, wherein the manufacturing method comprises a step of forming a tube-like braid made from electrically conductive strands such that ends of the strands are staggered in the longitudinal direction of the tube to be manufactured.

* * * * *